United States Patent [19]

Markham

[11] Patent Number: 4,693,257

[45] Date of Patent: Sep. 15, 1987

[54] NEEDLE ASPIRATION BIOPSY DEVICE WITH ENCLOSED FLUID SUPPLY

[76] Inventor: Charles W. Markham, 667 Snug Island, Clearwater Beach, Fla. 33515

[21] Appl. No.: 862,263

[22] Filed: May 12, 1986

[51] Int. Cl.$^4$ ............................................. A61B 10/00
[52] U.S. Cl. .................................. 128/752; 128/754; 604/44; 604/167; 604/187; 604/198
[58] Field of Search ............... 128/310, 749, 752, 753, 128/754, 757, 758; 604/43, 44, 164, 167, 173, 181, 187, 192, 198

[56] References Cited

U.S. PATENT DOCUMENTS

| | | | |
|---|---|---|---|
| 3,380,448 | 4/1968 | Sadove et al. | 604/263 |
| 3,610,226 | 10/1971 | Albisser | 604/27 |
| 4,457,313 | 7/1984 | Alter | 128/749 |

Primary Examiner—Henry J. Recla
Assistant Examiner—Randy Citrin
Attorney, Agent, or Firm—Ronald E. Smith; Harold D. Shall

[57] ABSTRACT

A needle aspiration biopsy device in the form of an external guide catheter having a distal end closed with a rapidly opening and closing valve. A syringe is disposed proximally of the guide catheter and has connected thereto a needle catheter which is telescopically received within the guide catheter. The needle catheter is made of an elongated tube mounting a needle at its distal end. A proximal seal seals the proximal end of the guide catheter and sealingly receives the needle catheter. The needle catheter extends to the distal end of the guide catheter and has a withdrawn position wherein the needle end thereof lies proximally of the valve in the distal end of the guide catheter and an extended position wherein the needle end thereof projects through and distally outwardly of the valve. A source of fluid is connected to the bore within the guide catheter at a location between the proximal seal and the distal valve. In a first embodiment the valve is made of a closed cell elastic plastic and the needle is of the non-coring type. In the second embodiment, the valve is of the normally closed flapper valve type.

10 Claims, 5 Drawing Figures

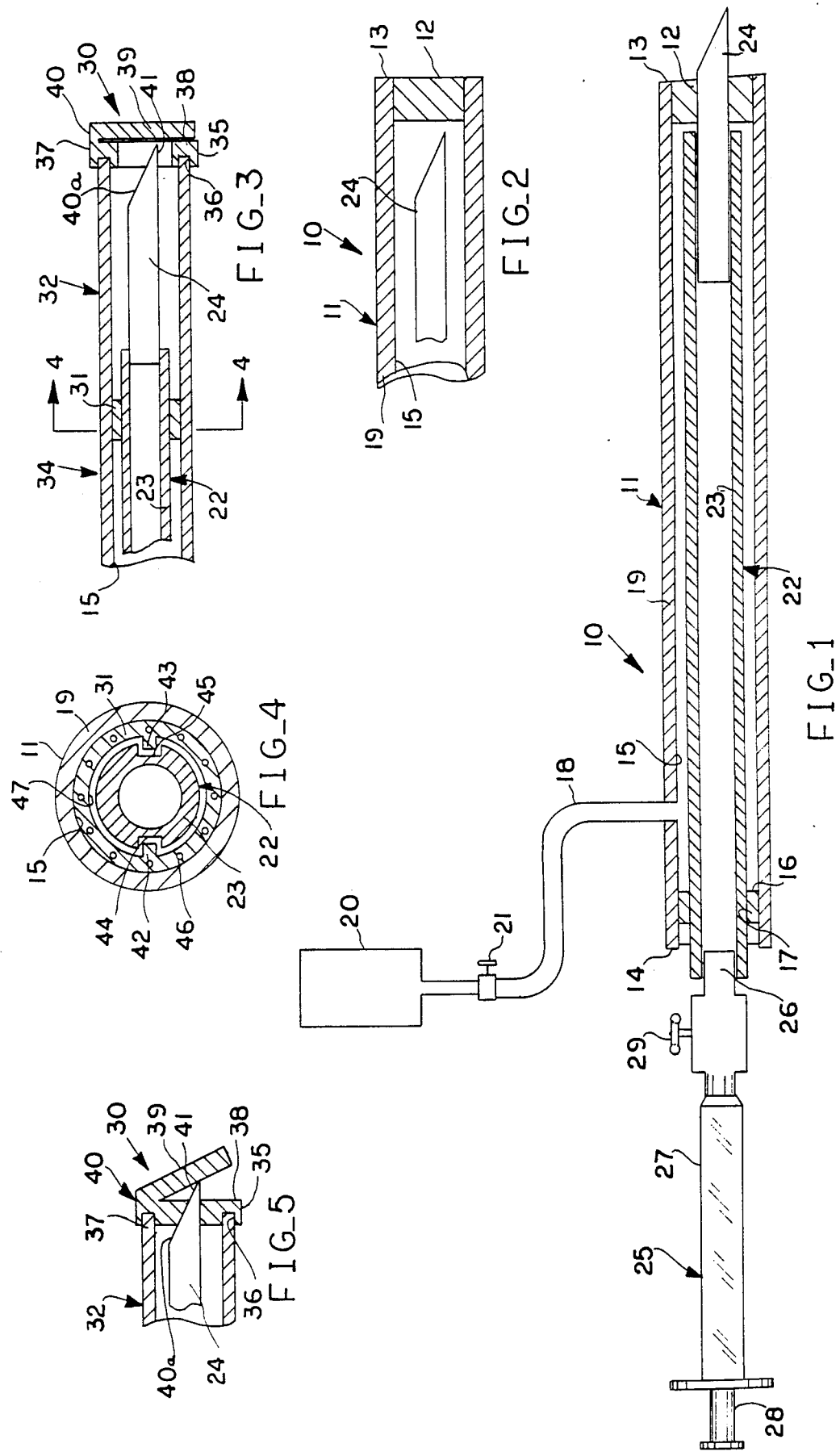

NEEDLE ASPIRATION BIOPSY DEVICE WITH ENCLOSED FLUID SUPPLY

BACKGROUND OF THE INVENTION

1. Field of the Invention

This invention relates generally to needle aspiration biopsy devices and more particularly to such a device having an enclosed surrounding fluid-filled catheter.

2. Description of the Prior Art

Utilizing an elongated needle to obtain a sample of body tissue or other material from within the body (be it man or animal) is well known. The simplest such device merely encompasses inserting in the body an endoscopic device, in the form of an elongated hollow tube such as a gastroscope, colonoscope or bronchoscope, utilizing a syringe with an elongated needle thereon, inserting the needle into the body through the endoscope and taking a tissue or a bacterial sample. The shortcomings of such devices are that the needle must be retracted completely out of the endoscope before the sample can be ejected from the needle for examination. If the needle is lengthy, there can be a substantial undesireable delay, or the sample can be lost or contaminated in transit. Further, if multiple samples are to be taken, the needle must be repeatedly inserted into the body through the endoscopic device, which certainly extends the time frame during which samples are taken to the detriment, inconvenience and discomfort of all involved. It is also known to insert through the endoscope a long handled brush, with the brush being used to withdraw the sample. Again this type of device results in delays and potential contamination of the sample.

A biopsy capsule arrangement is shown in U.S. Pat. No. 3,289,669 where a sample may be withdrawn from the body by means of a fluid flushing action through a tube; however, such a device does not lend itself to the fine needle biopsy techniques of the present invention and also utilizes a valving arrangement which is open during insertion of the device and also prior to sample taking so that whatever sample is obtained is likely to be contaminated.

U.S. Pat. No. 3,470,867 also shows a device for taking a sample; however, the same does not have a protective catheter with a valving device surrounding the needle nor does it disclose a means for flushing the sample back into the needle and syringe.

U.S. Pat. No. 4,235,244 discloses a long tube having a wax plug at its distal end, which tube is inserted into the body and then a sample taking device, in the form of a long handled brush, is inserted into the tube, knocks out the wax plug and then the brush is used to gather a sample which is taken back with the brush through the tube. This does not lend itself to repeated sample taking since the tube, once the plug is knocked out, is now open and contaminated. Further, the brush must be completely withdrawn from the tube to obtain the sample which can result in a substantial undesirable delay and the sample could be lost or contaminated in transit.

A search that was conducted in the U.S. Patent and Trademark Office prior to the filing of this disclosure located, in addition to the first two above-mentioned patents, the following patents of interest in the general field of this invention: U.S. Pat. Nos. 2,522,108; 4,139,009; and 3,526,219.

None of the above patents are relevant to the instant invention as claimed. No representation is made or intended that the prior art search was complete or that no better art than that listed is available.

SUMMARY OF THE INVENTION

The present invention relates to an aspiration biopsy device in the form of an external guide catheter which is suitable for insertion into the body through an endoscope; however, it is contemplated that the guide catheter could be directly inserted into a body opening or even used as a catheter in conjunction with procedures wherein the catheter is introduced into the body through a blood vessel.

At its distal end, the guide catheter is provided with a normally closed, but quick opening and closing distal valve means. In a first embodiment of this invention, the distal valve is formed of a closed cell highly resilient plastic such as closed cell polyurethane foam. In a second embodiment, the distal valve is of the normally closed flapper valve type.

An elongated needle catheter is inserted within the guide catheter. In the first embodiment, the distal end terminates in a non-coring needle such as one well known in the art as a type "A" bevel Monoject 25 or 27. At the proximal end of the guide catheter there is a proximal seal between the bore of the guide catheter and the periphery of the needle catheter; the needle catheter extending proximally of the guide catheter and the proximal seal accommodating relative telescoping action. The proximal end of the needle catheter is removably connected through an intermediate on-off valve to a sample taking syringe; however, the on-off valve can be eliminated. Connected to the guide catheter adjacent the distal end thereof at a location between the proximal seal and the distal valve is a supply tube which leads to a source of sample gathering solution; a preferred solution when a tissue sample is being taken being saline containing the conventional amount of Heparin, to prevent blood coagulation of the sample. An on-off valve may be provided in this supply tube.

In operation, prior to sample gathering, the needle of the first embodiment starts in a position proximally of the distal valve. The guide tube is inserted into the endoscope until the distal end thereof directly adjoins the area to be sampled. The guide tube is then held stationary and the needle catheter advanced distally so that the non-coring needle end thereof passes through the distal resilient plastic valve to the tissue location. The reason for a non-coring needle is that a coring needle might make a permanent opening in the distal valve. At this time a vacuum is drawn in the needle catheter by operation of the syring plunger and then the needle is used to shave off sample tissue. The supply tube to the saline solution is open and the needle containing the sample shavings is moved proximally back into the guide catheter. The vacuum in the needle catheter and syringe quickly draws saline solution into the needle where it carries the sample back to the syringe. The syrings valve is closed and the syringe removed from the needle catheter at which time the sample can be quickly ejected from the syringe for suitable examination by the pathologist. Since the needle catheter need not be withdrawn from the guide catheter to obtain the sample, the sample is obtained from the syringe very quickly. Additionally, a second syringe could be placed on the needle catheter and a second sample obtained, with the distal needle end merely again puncturing the valve.

In the second embodiment, instead of the guide catheter's distal valve being of a closed cell polyurethane plastic, it is made of a normally closed rapidly opening and closing valve such as a flapper valve made of polypropelene. When the needle catheter is advanced distally it opens the flapper valve and when the needle is moved proximally the flapper valve rapidly flaps closed aided by the vaccum from the syringe, so that the vacuum in the syringe can draw saline solution down the needle catheter as described with respect to the first embodiment. With the second embodiment, a non-coring needle is not required to be used since the needle is not puncturing the valve as in the first embodiement, and a coring or non-coring needle may be used.

The invention accordingly comprises the combination of elements, features of construction, and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a longitudinal sectional view of a first embodiment of this invention with portions thereof shown in full lines;

FIG. 2 is a fragmentary longitudinal sectional view of the embodiment shown in FIG. 1 in a different operative position;

FIG. 3 is a fragmentary longitudinal sectional view of a second embodiment of this invention;

FIG. 4 is a cross sectional view taken along line 4—4 in FIG. 3; and

FIG. 5 is a fragmentary longitudinal sectional view of the embodiment of FIG. 3 in a different operative position.

DETAILED DESCRIPTION OF THE PREFERRED EMBODIMENT

Referring now to the drawings and more particularly to FIGS. 1 and 2, a needle aspiration biopsy is shown generally at 10 and includes a cylindrical elongated guide catheter 11 having a distal end sealing valve 12 sealing the distal end 13 thereof. The valve 12 is made of a suitable resilient sealing plastic material such as a closed cell polyurethane foam; it is understood that other resilient sealing materials are suitable for this invention. From its distal end 13, the guide catheter 11 is elongated and terminates at its proximal end 14. Within the bore 15 of the catheter 11, adjacent the proximal end thereof is a proximal seal 16 having a central bore 17.

Intermediate the proximal seal 16 and the distal valve 12, a fluid supply means in the form of a tube 18 is secured to the wall 19 of the guide catheter 11 so as to be confluent with the bore 15 and the catheter. The remote end of the tube 18 is confluent with a supply reservoir 20, such as the well known collapsible plastic plasma bags. The supply tank 20 is filled with a suitable carrying solution such as saline solution with a small conventional amount of Heperin to prevent blood cutting in the tissue sample. A valve 21 of the on-off type is interposed in the tube 18 for when required to prevent the flow of solution.

Telescopically and sealingly received in the proximal seal 16 is the needle catheter 22 which comprises an elongated tubular portion 23 having sealingly secured in the distal end thereof a non-coring needle 24 such as a type "A" bevel Monoject 25 or 27. To the proximal end of the tubular portion 23 of the needle catheter 22 is removably sealingly secured the distal end of a syringe 25. The syringe 25 has its distal end 26 received in the needle catheter 22 and has an on-off valve 29 incorporated therein between its distal end 26 and the barrel portion 27 of the syringe 25. The syringe has a conventional plunger 28 at the proximal end thereof.

In FIG. 2, the device is shown with the needle 24 within the guide tube and disposed proximally of the valve 12, while in FIG. 1, the syringe 25 and needle catheter 22 have been advanced distally so that the needle 24 has penetrated the valve 12. At this time, the on-off valves 29 and 21 are both open so that the operator can move the plunger 29 distally thereby creating a vacuum in the distal end of the syringe and for the full length of the needle catheter 22, and solution from the tank 20 can flow toward the bore 15 of the guide catheter 11.

The needle 24 is then used to obtain a sample from the area to be examined, which sample will be drawn slightly into the needle 24 by the vacuum therein. The syringe is then moved proximally which moves the needle to the position shown in FIG. 2, i.e., proximally of the valve 12, and the vacuum within the needle and the syringe causes the fluid from the supply 20 to flow through the needle catheter 22 and into the syringe 25. The valves 21 and 29 are then closed and the distal end 26 of the syringe 25 is then removed from the proximal end of the needle catheter 22 so that the syringe can be conventionally emptied of the sample therein for examination by the desired method. The valve 29 need not be present, but it is convenient so that the sample is not inadvertently lost when the syringe is removed from the needle catheter.

Since the needle catheter 22 is still in place within the guide catheter and has been rinsed by the saline solution, another syringe can be placed in the needle catheter and a second sample quickly taken using the above procedure.

Since the needle 24 must only be moved a short distance from the outside to the inside of the valve 12, a very short time is involved from the time the sample is taken until the pathologist can examine the sample.

Referring now to FIGS. 3, 4 and 5, wherein a second embodiment of this invention is shown, the syringe 25 and the proximal end 14 of the guide catheter, the proximal end of the needle catheter and the fluid supply are the same. The only difference between this embodiment and that of FIGS. 1 and 2 is that the guide catheter 32 of the biopsy device 34 is provided with a flapper valve 30 instead of a closed cell plastic valve 12 as in FIGS. 1 and 2, and also the addition of a medially positioned porous support means 31 in the guide catheter for guiding the needle catheter.

More particularly, the flapper valve 30 is made of a suitable plastic such as polypropylene and has an annular body portion 35 in which is formed, as viewed in the drawings, an annular groove 36, which groove projects to the right from the left side of the body portion. The annular groove 36 is a snug pressed fit on the distal end of the guide catheter 32 and preferably securely bonded thereto. The body portion 35 has an annular distal facing sealing face 38 against which, as seen in FIG. 3, is sealingly abutted a flapper 39 of the flapper valve 30. The flapper 39 is hinged to the annular body portion 35 at a location shown at 40; which hinge is actually an integral part of the body portion 35 and the flapper 39. The hinge 40 extends a relatively short circumferential distance and polypropylene, as is well known, can function as a hinge. Further, the construction is such that the flapper 39 is normally biased to a closed position shown in FIG. 3 by the action of the hinge 40. As seen in FIG. 3, the needle 24 of the needle catheter 22 is disposed proximally of the valve 30, while in FIG. 5, the needle has commenced moving distally and is opening the flapper 39; it being understood that to reach the sample taking position, the needle 24 must be moved further distally than that shown in FIG. 5.

As seen in FIGS. 3 and 5, the bevel 40 of the needle 24 is slanted downwardly so that the tip 41 of the needle, when opening the flapper, engages the flapper 39 at its side opposite the hinge 40. If the needle taper were opposite from that shown, so that the needle would engage the flapper 39 adjacent the hinge 40 thereof, the flapper would be much more difficult to open and the needle might penetrate and damage the flapper and in the meantime the needle would be hung up in the flapper. To ensure that the tip 41 is disposed downwardly as seen in FIGS. 3 and 5, and is prohibited from rotating so that the tip assumes a different position, the porous support means 31 has a pair of diametrically opposed radially inwardly extending tangs 42 and 43 which are respectively received in diametrically opposed longitudinally extending grooves 44 and 45 formed in the periphery of the tubular portion 23. The porous support means is snugly received and suitably secured, as by bonding, to the bore 15 of the guide catheter 32. The porous support means has a plurality of axially extending openings 46 formed therein and the inner bore 47 thereof is spaced from the periphery of the tubular portion 23 of the needle catheter 22 at locations on the support means circumferentially intermediate the tangs 42 and 43. The openings 46 and the bore space provide for easy passage past the support means 31 of the saline solution from the tube 18 to the area of the needle tip 41.

Sample taking procedures of the embodiment of FIGS. 3-5 is the same as for FIGS. 1 and 2 except that the distal end of the guide catheter 32 of embodiment 3-5 must be at a sufficient distance from the sample area to allow the flapper 39 to open whereas with the embodiment of FIGS. 1 and 2, the valve 12 may be placed immediately adjacent the area to be sampled.

Although the description relates to the presently preferred embodiments, numerous modifications may be made without departing from the spirit of the invention as defined in the claims.

Since certain changes may be made in the above construction without departing from the scope of the invention, it is intended that all matters contained in the foregoing description, or shown in the accompanying drawings, shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, what is claimed is:

1. A sample taking device comprising,
   an external guide catheter having a distal and a proximal end,
   a rapidly opening and closing, normally closed, distal valve disposed at the distal end of said guide catheter,
   an elongated hollow needle catheter, having a distal and a proximal end, telescopically disposed in said external guide catheter and extending proximally therefrom,
   said guide catheter and needle catheter positioned in spaced apart, concentric relation to one another,
   an elongate space existing between said guide catheter and said needle catheter,
   sealing means at the proximal end of said guide catheter for sealingly connecting said guide catheter and said needle catheter while allowing relative telescopic movement to take place therebetween;
   an aspirating syringe removably connected to the proximal end of said needle catheter;
   a fluid source confluently connected to said guide catheter at a location intermediate said distal valve and said sealing means for supplying sample carrying fluid to said space,
   said needle catheter having a sample taking needle on the distal end thereof whereby upon distal movement of said needle catheter relative to said guide catheter, said sample taking needle moves outwardly of said guide catheter through said distal valve, at which time vacuum supplied to said needle by said aspirating syringe will slightly bring a sample within said needle and upon return of said needle past said distal valve, which valve immediately closes, and into said space, the sample carrying fluid is adapted to flow into said needle and is adapted to be carried therein to said aspirating syringe,
   said distal valve operative to retain said sample carrying fluid within said device at all times,
   and said syringe and said fluid source being independent elements of said device.

2. A device according to claim 1 wherein said distal valve is made of a resilient plastic which is punctured by said sample taking needle upon distal movement of said needle past said distal valve and which plastic resiliently closes upon proximal movement of said needle to a position within said space.

3. A device according to claim 2 wherein said distal valve is made of a closed cell resilient plastic.

4. A device according to claim 3 wherein said aspirating syringe has a barrel portion and a connecting portion to connect said barrel portion to said needle catheter and said syringe has an on-off valve disposed between said barrel portion and said connecting portion.

5. A device according to claim 3 wherein said fluid source includes an on-off valve for controlling the flow of fluid from said fluid source to said space.

6. A device according to claim 2 wherein said aspirating syringe has a barrel portion and a connecting portion to connect said barrel portion to said needle catheter, and said syringe has an on-off valve disposed between said barrel portion and said connecting portion.

7. A device according to claim 2, wherein said fluid source includes an on-off valve for controlling the flow of fluid from said fluid source to said space.

8. A sample taking device for rapidly taking a non-contaminated specimen comprising,
   an external guide catheter having a bore,
   a needle catheter, having a needle end, disposed in said external guide catheter and terminating distally in a needle and extending from a location proximally of said guide catheter and being long enough so that its needle end can be moved distally of said guide catheter while a portion of said needle catheter still projects proximally from said guide catheter, a rapidly opening and closing distal valve closing a distal end of said guide catheter, sealing means sealing a proximal end of said guide catheter and telescopically sealingly engaging said needle catheter, a fluid source means confluent with the bore of said guide catheter between said sealing means and said distal valve, said bore of said guide catheter defining an elongate space surrounding said needle catheter which space may be occupied by fluid from said fluid source means, an aspirating syringe removably connected to a proximal end of said needle catheter, said distal valve operative to maintain said fluid within said device at all times, and said syringe and fluid source means being independent members of said device.

9. A device according to claim 8 wherein said distal valve is a resilient plastic plug which is punctured by the needle on said needle catheter upon the latter moving distally relative to the distal valve.

10. A device according to claim 9 wherein said resilient plastic plug is made of a closed cell resilient polyurethane foam.

* * * * *